(12) United States Patent
Koppel et al.

(10) Patent No.: US 6,768,785 B2
(45) Date of Patent: Jul. 27, 2004

(54) CALIBRATION AND ALIGNMENT OF X-RAY REFLECTOMETRIC SYSTEMS

(75) Inventors: Louis N. Koppel, Menlo Park, CA (US); Craig E. Uhrich, Redwood City, CA (US); Jon Opsal, Livermore, CA (US)

(73) Assignee: Therma-Wave, Inc., Fremont, CA (US)

(*) Notice: Subject to any disclaimer, the term of this patent is extended or adjusted under 35 U.S.C. 154(b) by 0 days.

(21) Appl. No.: 10/643,348

(22) Filed: Aug. 19, 2003

(65) Prior Publication Data

US 2004/0052330 A1 Mar. 18, 2004

Related U.S. Application Data

(62) Division of application No. 10/124,776, filed on Apr. 17, 2002, now Pat. No. 6,643,354, which is a division of application No. 09/527,389, filed on Mar. 16, 2000, now Pat. No. 6,453,006.

(51) Int. Cl.[7] .............................................. G01N 23/20
(52) U.S. Cl. ............................ 378/70; 378/54; 378/89
(58) Field of Search .............................. 378/70, 71, 50, 378/53, 54, 82, 84, 89

(56) References Cited

U.S. PATENT DOCUMENTS

| | | | | |
|---|---|---|---|---|
| 4,064,440 | A | * 12/1977 | Roder | 378/57 |
| 4,727,562 | A | * 2/1988 | Belanger | 378/98.4 |
| 5,042,951 | A | 8/1991 | Gold et al. | 356/369 |
| 5,412,473 | A | 5/1995 | Rosencwaig et al. | 356/351 |
| 5,475,728 | A | 12/1995 | Smith et al. | 378/81 |
| 5,619,548 | A | 4/1997 | Koppel | 378/70 |
| 5,848,122 | A | * 12/1998 | Kurtz | 378/80 |
| 5,878,106 | A | 3/1999 | Fujiwara | 378/79 |
| 5,923,720 | A | 7/1999 | Barton et al. | 378/84 |
| 6,041,098 | A | 3/2000 | Touryanski et al. | 378/70 |
| 6,069,934 | A | 5/2000 | Verman et al. | 378/73 |
| 6,381,303 | B1 | * 4/2002 | Vu et al. | 378/46 |
| 2002/0001365 | A1 | * 1/2002 | Mazor et al. | 378/89 |

FOREIGN PATENT DOCUMENTS

| | | | |
|---|---|---|---|
| DE | 144 956 | 11/1980 | G01B/15/02 |
| JP | 20011116705 | 4/2001 | G01N/23/207 |
| WO | WO 92/08104 | 5/1992 | G01B/11/24 |

OTHER PUBLICATIONS

K. Sakurai et al., "Fourier Analysis of Interference Structure in X–Ray Specular Reflection from Thin Films," *Jpn. J. Appl. Phys.*, vol. 31, 1992, pp. L113–L115.

K.N. Stoev et al., "Review on grazing incidence X–ray spectrometry and reflectometry," *Spectrochimica Acta Part B*, vol. 54, 1999, pp. 41–82.

N. Wainfan et al., "Density Measurements of Some Thin Copper Films," *Journal of Applied Physics*, vol. 30, No. 10, Oct. 1959, pp. 1604–1609.

J.P. Sauro et al., "Some Observations on the Interference Fringes Formed by X Rays Scattered from Thin Films," *Physical Review*, vol. 143, No. 1, Mar. 1966, pp. 439–443.

K. Sakurai et al., "Analysis of thin films by X–ray scattering at grazing incidence," *SPring–8 User Experiment Report No. 2 (1998 A)*, Mar. 1999, p. 162.

* cited by examiner

*Primary Examiner*—Craig E. Church
*Assistant Examiner*—Irakli Kiknadze
(74) *Attorney, Agent, or Firm*—Stallman & Pollock LLP (57) ABSTRACT

The present invention relates to the calibration and alignment of an X-ray reflectometry ("XRR") system for measuring thin films. An aspect of the present invention describes a method for accurately determining $C_0$ for each sample placement and for finding the incident X-ray intensity corresponding to each pixel of a detector array and thus permitting an amplitude calibration of the reflectometer system. Another aspect of the present invention relates to a method for aligning an angle-resolved X-ray reflectometer that uses a focusing optic, which may preferably be a Johansson crystal. Another aspect of the present invention is to validate the focusing optic. Another aspect of the present invention relates to the alignment of the focusing optic with the X-ray source. Another aspect of the present invention concerns the correction of measurements errors caused by the tilt or slope of the sample. Yet another aspect of the present invention concerns the calibration of the vertical position of the sample.

10 Claims, 11 Drawing Sheets

REFLECTED BEAM RAW DATA
FIG. 3

FIG. 4

$C_O$-PLOTTED INCIDENT & REFLECTED BEAMS

FIG. 5

INCIDENT BEAM PROFILES AT DIFFERENT RUN-OUT DISTANCES

FIG. 6

DETERMINING THE FOCAL LOCATION

FIG. 7

INCIDENT BEAM PROFILE FORMED BY A GRID MASK

FIG. 8

SHADOW OF A FINE WIRE IN AN INCIDENT BEAM PROFILE

CALIBRATION AND ALIGNMENT OF X-RAY REFLECTOMETRIC SYSTEMS

RELATED APPLICATIONS

This application is a divisional of application Ser. No. 10/124,776, filed Apr. 17, 2002, now U.S. Pat. No. 6,643,354, which is a divisional of application Ser. No. 09/527,389, filed Mar. 16, 2000 (issued U.S. Pat. No. 6,453,006 B1).

FIELD OF THE INVENTION

X-ray reflectometry is a technique for measuring the thicknesses of thin films in semiconductor manufacturing and other applications. In order to maximize accuracy with this technique, it is necessary to precisely calibrate and align elements of the X-ray reflectometry system and the present invention relates to methods for achieving this.

BACKGROUND OF THE INVENTION

There is considerable need to accurately measure the thicknesses of thin films, particularly in the semiconductor manufacturing industry. One method for making such measurements is an X-ray reflectometry technique ("XRR") which relies on measuring the interference patterns of X-rays scattered from a thin film sample. With XRR the reflectivity of a sample is measured at X-ray wavelengths over a range of angles. These angles typically range from zero degrees, or grazing incidence along the surface of the sample, to a few degrees. From the X-ray interference pattern, properties of the sample such as material composition and thickness can be inferred.

In a recent development, simultaneous measurements of the sample reflectivity over a range of angles are accomplished by illuminating the sample with a focused beam and then detecting the reflected X-rays with a position sensitive detector such as a photodiode array.

XRR has several advantages over techniques using visible light. One such advantage is that XRR makes it possible to measure the thickness of ultra-thin films whose thicknesses are on the order of 30 angstroms or less. Visible light is not suitable for the study of such ultra-thin films using interference patterns because of its wavelength. However, an XRR system may preferably use radiation at wavelengths of about 1.5 angstroms, which radiation creates suitable interference patterns even when probing such ultra-thin films. In addition, XRR may suitably be used where the film is composed of a material that is opaque to light, such as a metal or metal compound. Finally, XRR may suitably be used to measure the density and thickness of films composed of materials that have a low dielectric constant and a correspondingly low index of refraction, such as certain polymers, carbon fluoride compounds, and aerogels.

Figure 1:
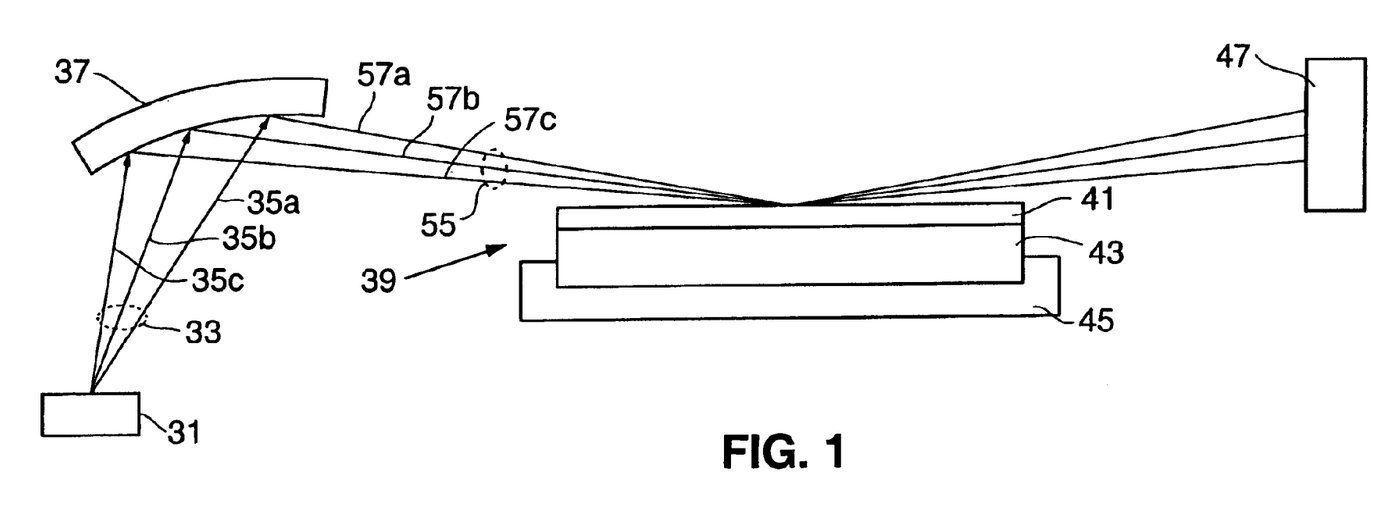
FIG. 1 shows a preferred X-ray reflectometry system.

A preferred XRR technique is described in U.S. Pat. No. 5,619,548, issued Apr. 8, 1997, which is hereby incorporated by reference in its entirety. FIG. 1 illustrates this preferred technique.

Referring to FIG. 1, the preferred X-ray scattering system includes an X-ray source 31 producing an X-ray bundle 33 that comprises a plurality of X-rays shown as 35a, 35b, and 35c. An X-ray reflector 37 is placed in the path of the X-ray bundle 33. The reflector 37 directs the X-ray bundle 33 onto a test sample 39 held in a fixed position by a stage 45, and typically including a thin film layer 41 disposed on a substrate 43. Accordingly, a plurality of reflected X-rays, 57a, 57b, and 57c concurrently illuminate the thin film layer 41 of the test sample 39 at different angles of incidence.

Figure 2:
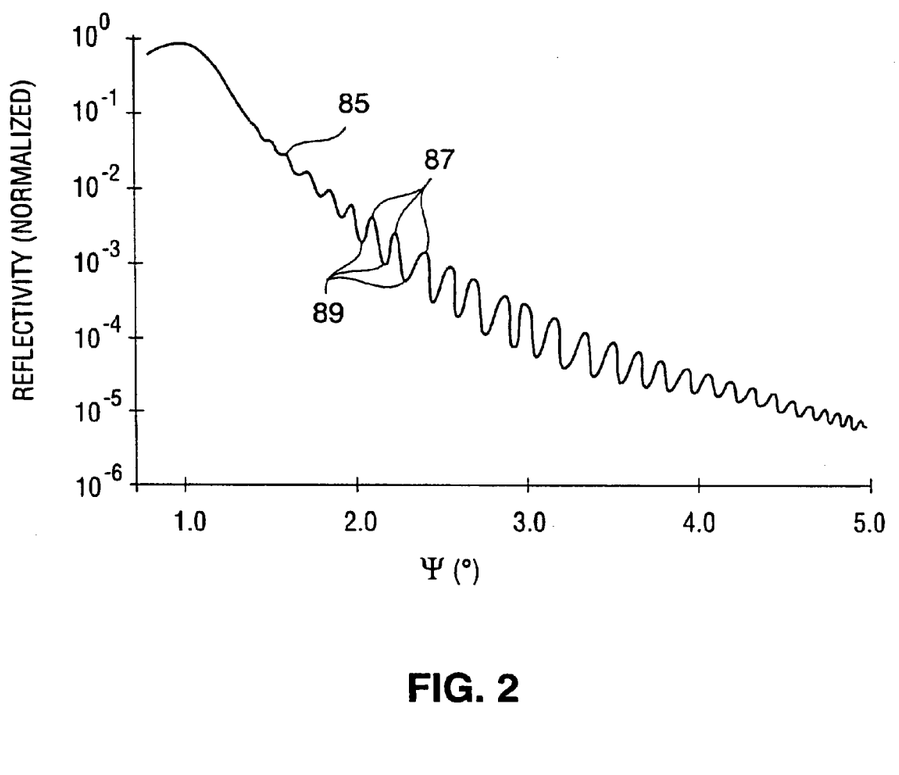
FIG. 2 shows a normalized graph of sample X-ray reflectivity as a function of the angle of incidence to the sample.

The X-ray reflector 37 is preferably a monochromator. The diffraction of the incident bundle of X-rays 33 within the single-crystal monochromator allows only a narrow band of the incident wavelength spectrum to reach the sample 39, such that the Brag condition is satisfied for this narrow band. As a result, the plurality of X-rays 57a, 57b, and 57c, which are directed onto the test sample 39, are also monochromatic. A detector 47 is positioned to sense X-rays reflected from the test sample 39 and to produce signals corresponding to the intensities and angles of incidence of the sensed X-rays. FIG. 2 depicts an example of a graph of data from the detector 47 showing a normalized measure of the reflectivity of the sample as a function of the angle of incidence to the surface of the sample 39. A processor is connected to the detector to receive signals produced by the detector in order to determine various properties of the structure of the thin film layer, including thickness, density and smoothness.

In order to maximize the accuracy of the X-ray measurements, it is necessary to precisely calibrate and align the XRR system. The present invention relates to techniques for doing this.

SUMMARY OF THE INVENTION

Figure 3:
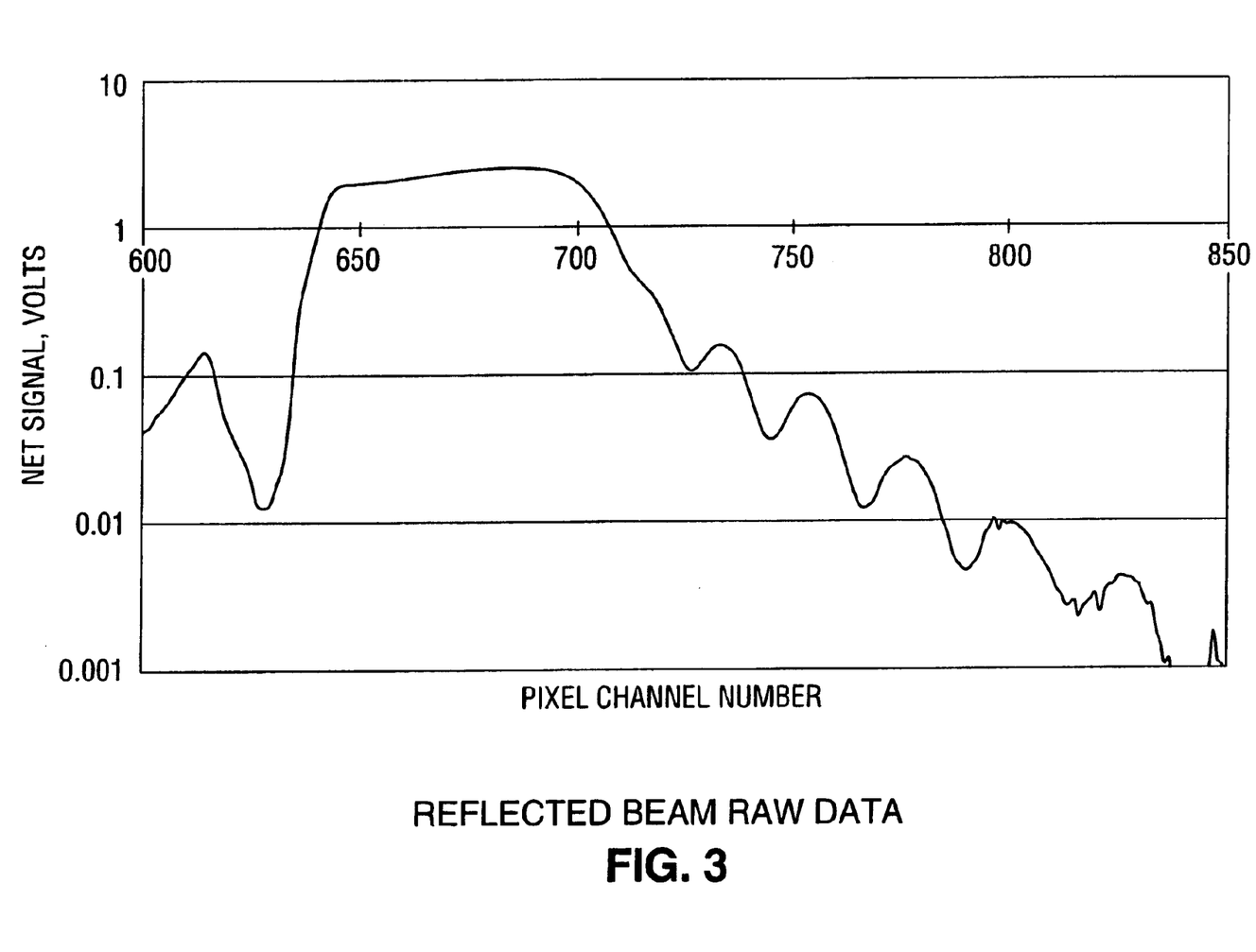
FIG. 3 shows a graph of raw data from a position sensitive detector in an XRR system giving signal strength as a function of pixel number.

One object of the present invention relates to the calibration of the detector 47. In order to properly interpret the raw data graphed in FIG. 3, it is necessary to determine which pixel $C_0$ lies on the extended plane of the sample 39. In addition it is necessary to find the intensity of the incident, unreflected X-ray corresponding to each pixel in order to be able to normalize the reflected X-ray intensity readings on a point-by-point basis. An aspect of the present invention describes a method for accurately determining $C_0$ for each sample placement and for finding the incident X-ray intensity corresponding to each pixel and thus permitting an amplitude calibration of the reflectometer system.

Another object of the present invention relates to a method for aligning an angle-resolved X-ray reflectometer that uses a focusing optic, which may preferably be a Johansson crystal. In accordance with the present invention, the focal location may be determined based on a series of measurements of the incident beam profile at several different positions along the X-ray optical path.

Another object of the present invention is to validate the focusing optic. It is important that the focusing optic forms an X-ray beam of uniform and predictable convergence. This is necessary in order to achieve an accurate one-to-one correspondence between the pixel location on the detector and the angle of reflection of X-rays from the sample. A validation of the optics may be performed using a grid mask consisting of regularly spaced openings and opaque bars in order to observe the accuracy of optic shaping.

Another object of the present invention relates to the alignment of the focusing optic with the X-ray source. For example, in the case of an X-ray tube source, achieving the best angular resolution for the reflectometer requires that the line focus of the X-ray tube and the bend axis of the focusing optic be coaligned so as to be accurately parallel. A method for checking this coalignment is to place a fine wire between the X-ray source and the optic and observe the shadow of the wire in the beam profile formed by the optic.

Another object of the present invention concerns the correction of measurements errors caused by the tilt or slope of the sample.

Yet another object of the present invention concerns the calibration of the vertical position of the sample. Changes in the sample height lead to shifts in the location of the reflected beam, so that the vertical sample position must be calibrated if an accurate measurement is to be made.

DETAILED DESCRIPTION OF THE INVENTION

One aspect of the present invention relates to the calibration of the detector 47. For convenience, this aspect of the present invention will be described with respect to the preferred type of detector, a multi-channel photo-diode array, but the same technique could be applied to other types of spatially sensitive detectors capable of resolving the reflected X-rays from the sample 39. The detector yields raw data showing the intensity of the reflected X-rays as a function of the detector channel ("pixel") number, as shown graphically in FIG. 3. In order to properly interpret the raw data graphed in FIG. 3, it is necessary to determine which pixel $C_0$ lies on the extended plane of the sample 39. In addition it is necessary to find the intensity of the incident, unreflected X-ray corresponding to each pixel in order to be able to normalize the reflected X-ray intensity readings on a point-by-point basis. This calibration is necessary because the reflection efficiency of the sample for each angle of incidence is actually calculated as a ratio of reflected and incident signal amplitudes. This aspect of the present invention describes a method for accurately determining $C_0$ for each sample placement and for finding the incident X-ray intensity corresponding to each pixel and thus permitting an amplitude calibration of the reflectometer system.

The relationship between the reflection angle θ and the pixel number C is given by θ=arctangent $(p(C-C_0)/D)$, where p is the pixel spacing ("pitch") of the detector, D is the distance between the illuminated part of the sample and the detector, and $C_0$ is the pixel number at which the extended plane of the sample intercepts the detector. The parameters p and D are customarily known with sufficient accuracy from the construction details of the detector (for the pitch p) and the reflectometer (for the distance D). The value $C_0$, however, can vary from one sample placement to another, and must be determined (or at least verified) for each measurement.

Figure 4:
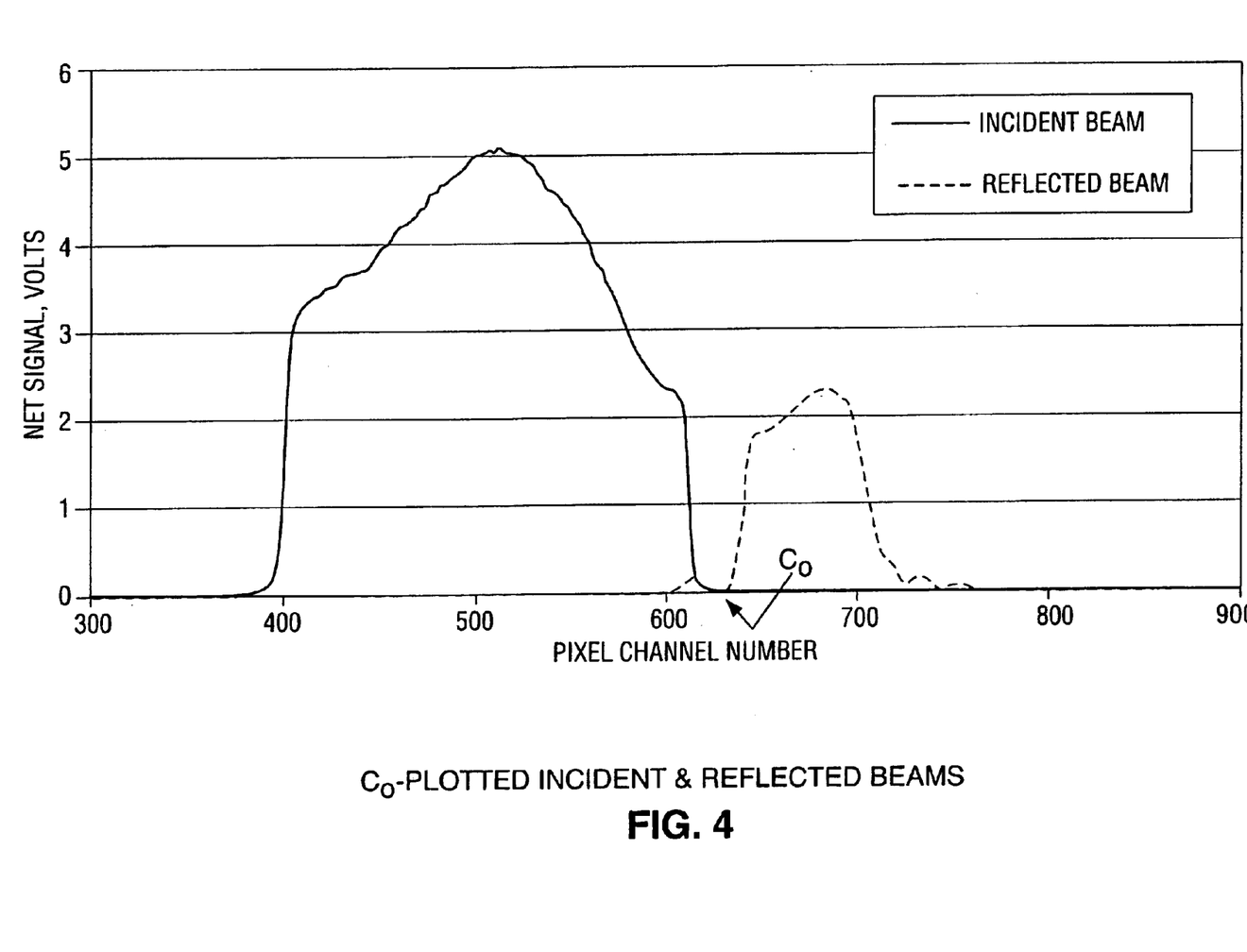
FIG. 4 shows graphs of both the incident X-ray beam and the reflected X-ray beam (dashed lines) as received by the position sensitive detector in an XRR system.
Figure 14:
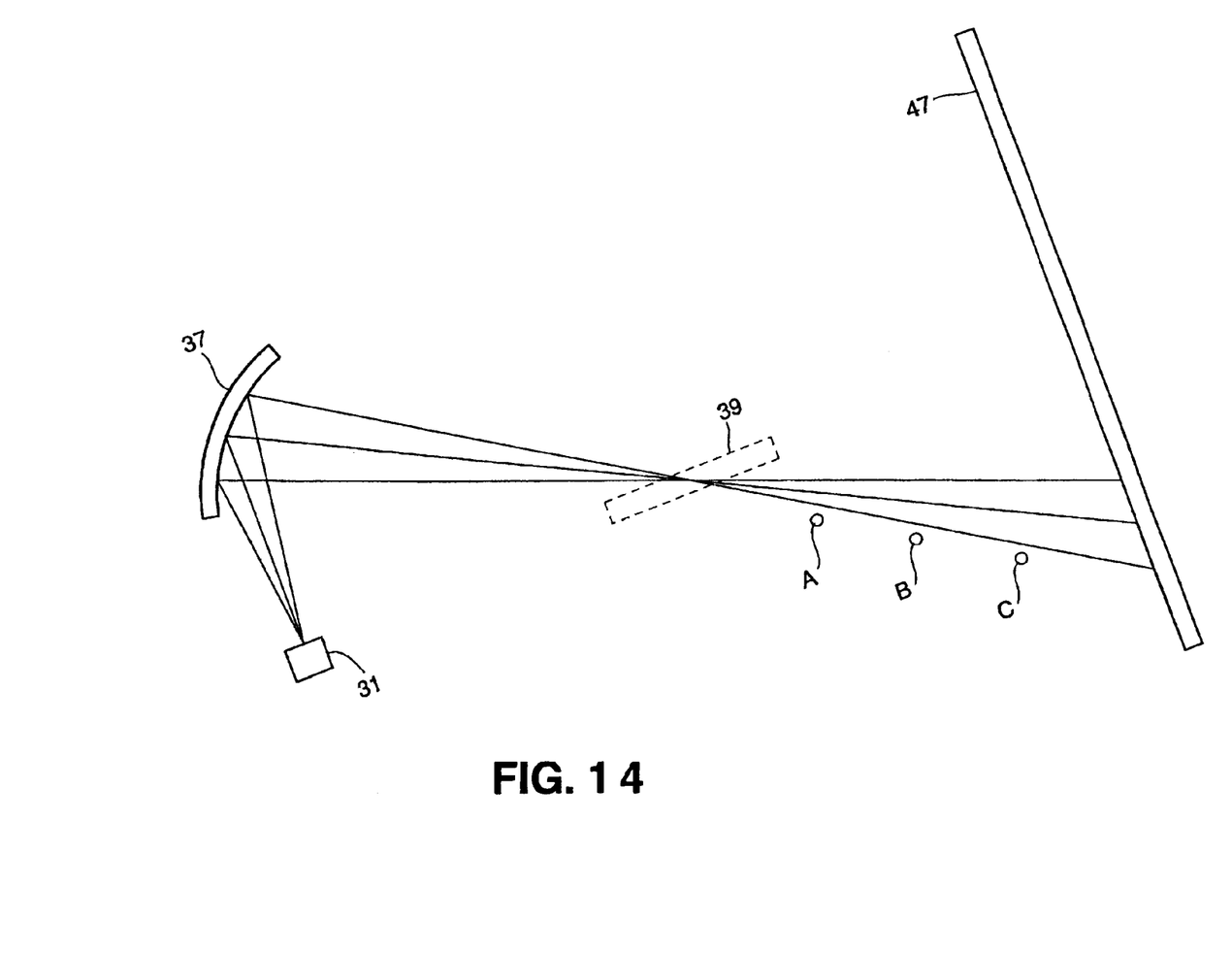
FIG. 14 shows a method for finding the intensities of the unattentuated X-rays at each angle of incidence in order to be able to properly normalize the measurements of the X-ray detector.

In order to accomplish these angular and amplitude calibrations of the reflectometer, a detector is used that extends below the plane of the sample as well as above it. The use of such a detector 47' is shown in FIG. 14, where the dashed lines indicate that the sample 39 has been removed from the X-ray pathway. By occasionally removing the sample from the X-ray pathway, the unattenuated incident beam can then be detected on the lower portion of the detector. In this way the incident beam pattern can be recorded and viewed side-by-side with the reflected beam, as shown in FIG. 4. $C_0$ is a point of symmetry that lies midway between the leading edges of the incident and reflected patterns. An approximate location for $C_0$ is shown in FIG. 4. The reason this is so is that the reflection from the sample is nearly total for a range of very small angles of incidence that are less than the critical angle. For this limited range of angles, then, the incident and reflected patterns should be symmetrical about $C_0$. This means that $C_0$ is represented by the pixel number about which the incident beam pattern can be "folded over" to overlap the reflected pattern. The folding is correct and $C_0$ is properly identified when the leading edge of the reflected pattern in the region of total reflection falls exactly over the corresponding leading edge of the incident profile.

$C_0$ can accordingly be located in the following manner. First, one locates the peak of the reflected signal. Because the sample reflectivity drops off very quickly at angles greater than the critical angle, the peak of the reflected profile lies close to the critical angle and serves to identify an approximate upper bound for the region of the reflected profile that is of interest. To avoid getting data from beyond the critical angle, the upper limit for the region of interest is preferably set to 90% of the peak of the reflected beam. Second, one locates the point where the incident and reflected profile signals cross. This point is approximately the location of $C_0$ and serves to identify an approximate lower bound for the region of the reflected profile that is of interest. Because data from very weak signals tends to be bad and may be significantly corrupted by noise, the lower limit is preferably set to a signal level that is twice the level at which the two signals cross. Third, one chooses various signal levels in the region of the reflected profile curve that is of interest, and draws horizontal lines between the reflected and incident profile curves at those signal levels. Fourth, one finds the midpoints of the horizontal lines between the two profiles drawn in the previous step. Fifth, one calculates the average center pixel $C_0$ from this set of midpoints after excluding outlying data points.

Figure 5:
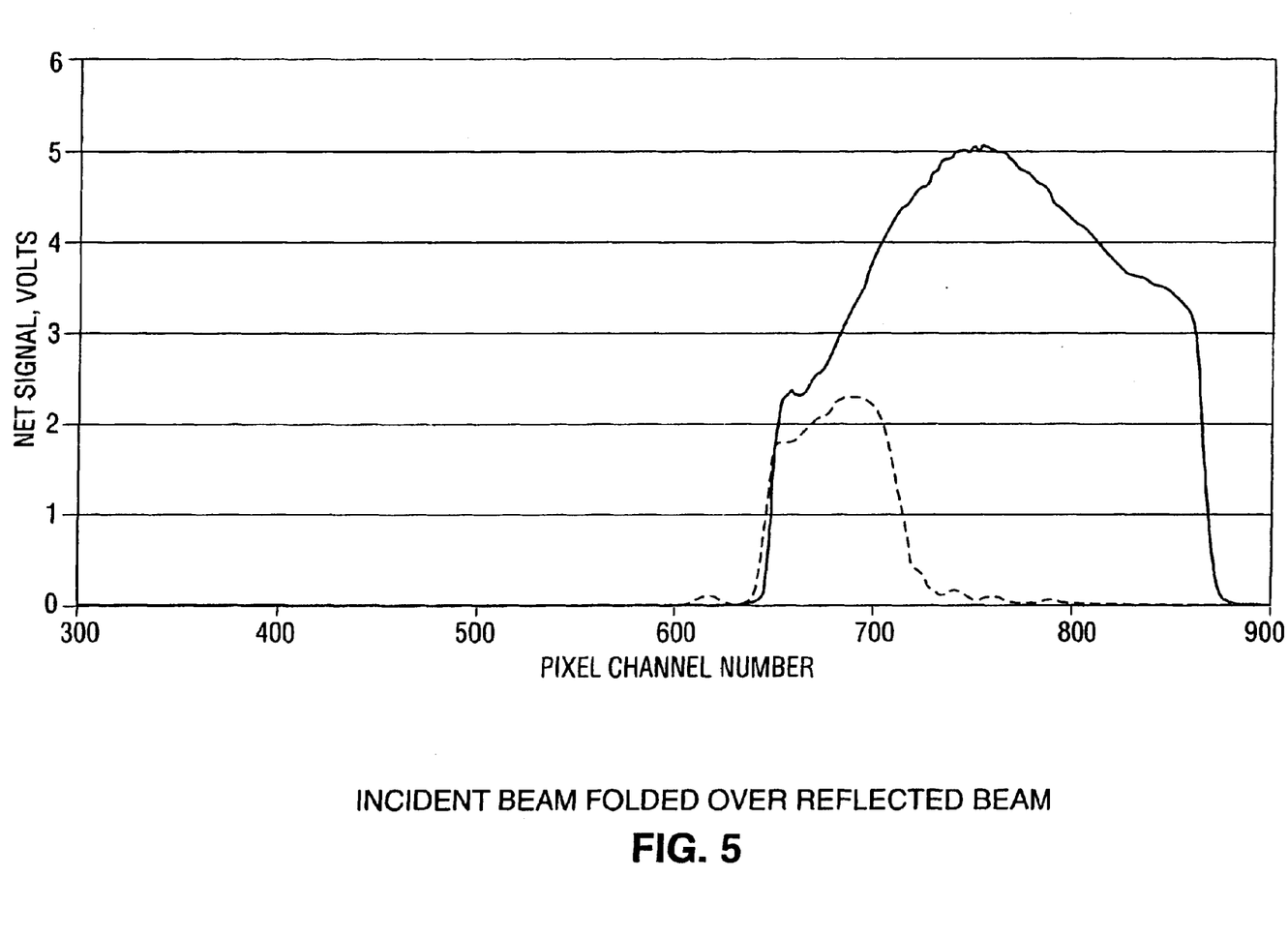
FIG. 5 shows a graph where the measurements of the pixels sensing the incident X-ray beam have been inverted through a calculated pixel $C_0$ so that the incident beam is "folded over" the reflected X-ray beam as measured by the position sensitive detector in an XRR system.

Once the point of symmetry $C_0$ has been determined, the incident beam can be folded over the reflected beam by inverting the pixel array associated with the incident profile through the point $C_0$. These operations produce a graph such as that shown in FIG. 5. A normalized reflectivity is then calculated by dividing the raw values in the reflected profile by the corresponding incident profile values on a point-by-point basis. In this way the reflected profile data from the detector may be properly interpreted.

Another aspect of the present invention relates to a method for aligning an angle-resolved X-ray reflectometer that uses a focusing optic, which may preferably be a Johansson crystal. It is necessary to determine where in space the focused image of the X-ray source region falls, in order to establish the distance D between the focused image and the detector. As discussed above, this parameter is used to match pixels to reflection angles via the reflection angle correlation: $\theta = \arctan(p(C-C_o)/D)$. It is also desirable to know the focal location, because this is the preferred position of the front surface of the thin film sample being examined by the reflectometer in order to minimize that X-ray beam "footprint" or irradiated area on the surface of the sample.

Figure 6:
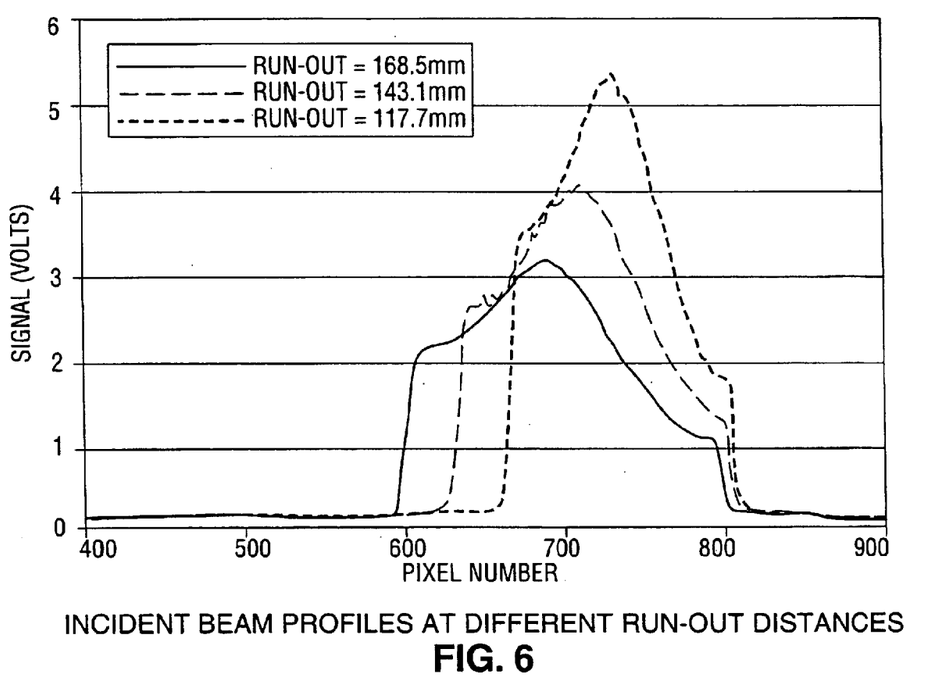
FIG. 6 shows graphs of the incident beam profile with a detector placed at three different "run-out" distances from the nominal focal location of the X-ray optic.
Figure 7:
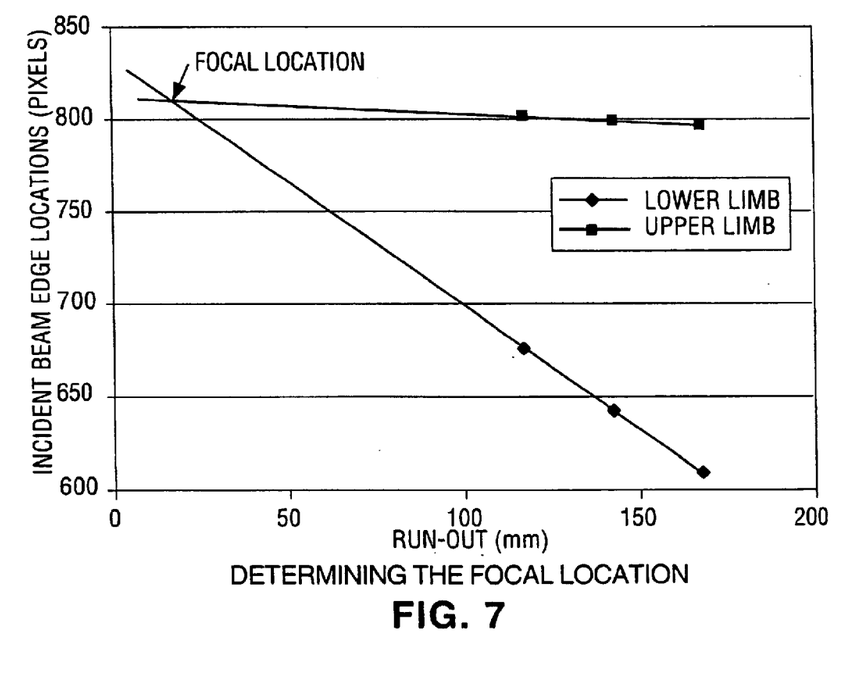
FIG. 7 shows a plot of the locations of the upper and lower limbs of the beam profile graphs shown in FIG. 6 as a function of "run-out" distance.

In accordance with the present invention, the focal location may be determined based on a series of measurements of the incident beam profile at several different positions along the X-ray optical path. A measurement series of this sort is shown graphically in FIG. 6, in which the incident beam profile is detected at several values of "run-out" distance from the nominal focal location. (Points "A", "B", and "C" of FIG. 14 illustrate this methodology.) In FIG. 6 the width of the profile decreases as the detector location approaches the nominal focal location. The actual focal location is the position in space at which the profile width extrapolates to zero. In FIG. 7 the locations of the shoulders of the incident beam profiles are plotted and denoted as the lower and upper limbs. The focal location is then the point at which the lower and upper limbs converge.

In order to find this convergence point, the incident beam edge data collected at the various run-out locations may be fitted by linear regression techniques to obtain a pair of algebraic relations describing the lower and upper edge locations as a function of run-out distance. The actual focal location is then determined by solving algebraically for the intersection point of the two traces. In the case shown in FIG. 6, we find that the actual focal location is about 15 mm closer to the detector than the nominal value. The edge trace data also shows the minimum and maximum angles of incidence contained in the converging fan of X-rays that expose the sample. These angular values are reflected in the slopes of the traces.

Another aspect of the present invention relates to the validation of the focusing optic. It is important that the focusing optic forms an X-ray beam of uniform and predictable convergence. This is necessary in order to achieve an accurate one-to-one correspondence between the pixel location on the detector and the angle of reflection of X-rays from the sample. A validation of the optics may be performed using a grid mask consisting of regularly spaced openings and opaque bars in order to observe the accuracy of optic shaping.

Figure 8:
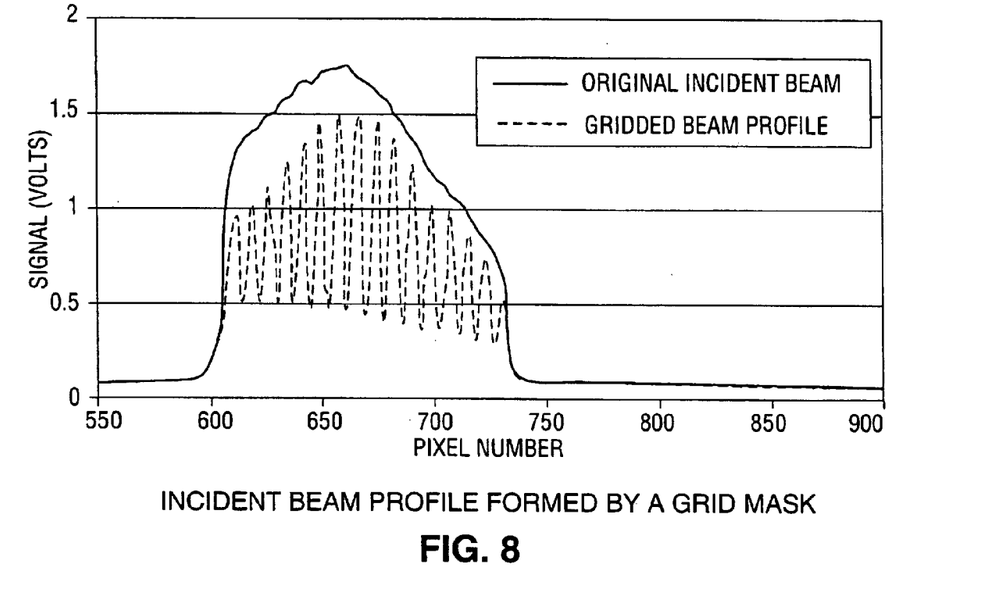
FIG. 8 shows a graph of both the original incident X-ray beam and the profile of the incident X-ray beam after it has passed through a grid as measured by a detector.

In order to accomplish this, the grid mask is placed across the X-ray beam path between the X-ray source and the optic, and the shadow pattern formed by the mask is detected at a position downstream from the optic. Data of this sort, formed by a mask having regularly spaced 75 μm-wide openings and bars, is shown in FIG. 8. Deviations from these locations are produced by distortions of the optic from its intended figure. If the optic is correctly formed, the features of the observed grid pattern, its minima and maxima, should fall in predictable locations based on the opening and bar spacings of the grid. In this way the focusing optic may be validated.

Figure 9:
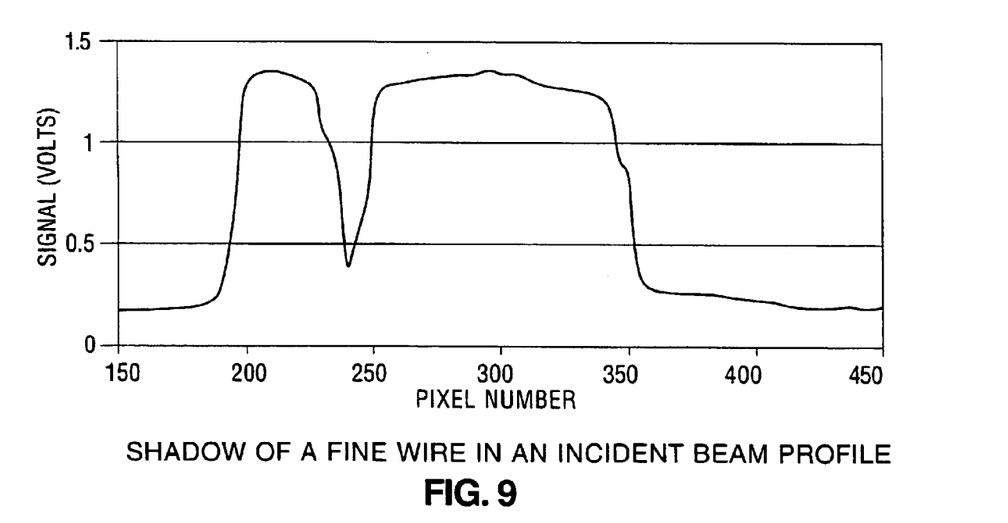
FIG. 9 shows a graph of the incident X-ray beam profile where the beam path is partially blocked by a wire.

Another aspect of the present invention relates to the alignment of the focusing optic with the X-ray source. For example, in the case of an X-ray tube source, achieving the best angular resolution for the reflectometer requires that the line focus of the X-ray tube and the bend axis of the focusing optic be coaligned so as to be accurately parallel. A method for checking this coalignment is to place a fine wire between the X-ray source and the optic and observe the shadow of the wire in the beam profile formed by the optic. A pattern of this sort is shown in FIG. 9. One can use a pinhole photograph of the X-ray source to determine the orientation of its line focus and to prealign the wire to that orientation. The width of the wire's shadow is then a measure of the tilt misalignment of the optic with respect to the tube's line focus. An accurate coalignment can then be obtained by manipulating the optic's tilt so as to minimize the width of the shadow.

Figure 10A:
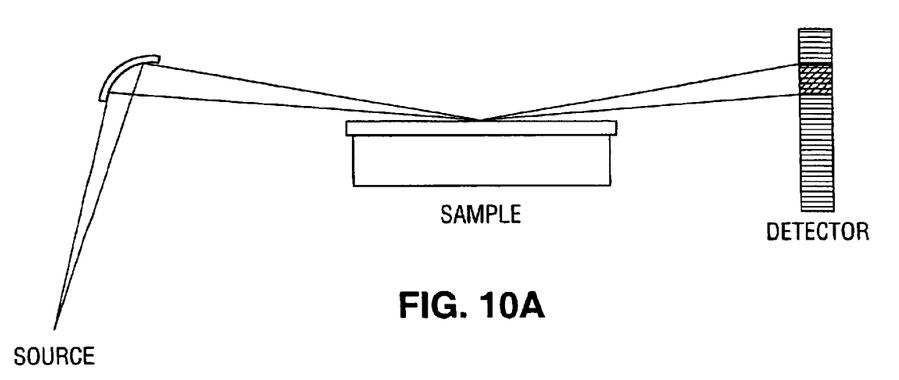
FIG. 10a shows the relationship of X-ray angle of incidence and detector pixels in an XRR system when the sample is not tilted.
Figure 10B:
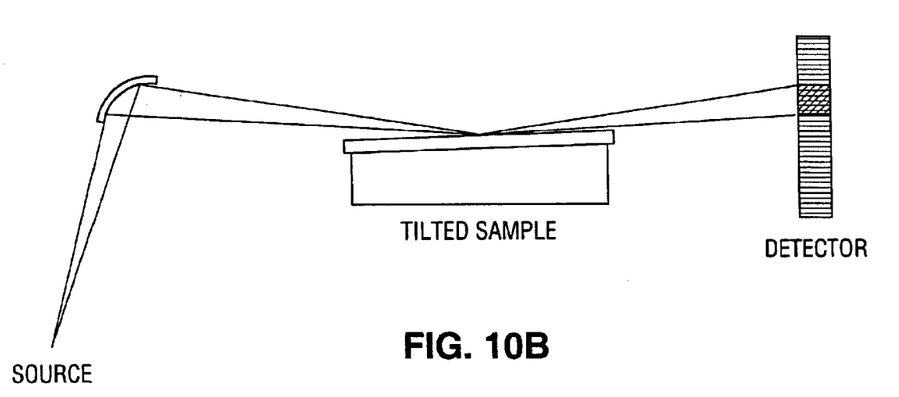
FIG. 10b shows the altered relationship of X-ray angle of incidence and detector pixels in an XRR system when the sample is tilted.

Another aspect of the present invention concerns the correction of measurements errors caused by the tilt or slope of the sample. The slope of the sample is a critical parameter. Small variations in the sample flatness or the mechanical slope in the supporting stage can lead to variations in this plane as shown in FIGS. 10a and 10b. As these figures show, changes in the sample tilt change the direction of the reflected beam. In particular, tilts along the direction of the beam travel ("pitch") cause the beam to shift up or down on the detector. Essentially, the rays at each incident angle are redirected to different pixels. If such tilt shifts are not accounted for, the calculated angular reflectivity will be wrong.

Errors of less than 0.005° in the sample tilt can change the film thickness calculations by as much as a few angstrom, which is an amount that is greater than the inherent sensitivity of the X-ray reflectometer measurement. In other words, sample tilts in this range can be the major source of measurement error. To limit the stage tilt to a tolerable level of, say, 0.001° requires less than 1.8 microns of vertical error over a 4" radius (a typical radius for a silicon wafer).

Tilt in a direction perpendicular to the beam direction ("roll") will also alter the direction of the reflected beam. In this case, the predominant effect is a side-to-side shift of the beam on the detector. Since the beam strikes the same pixel range, however, the relationship between pixel and incidence angle is preserved. Thus, roll is a less critical phenomenon than pitch. Still, irregularities in the beam shape could give rise to measurement errors if the roll were sufficiently severe to alter the intensity of the detected portion of the beam.

Figure 11:
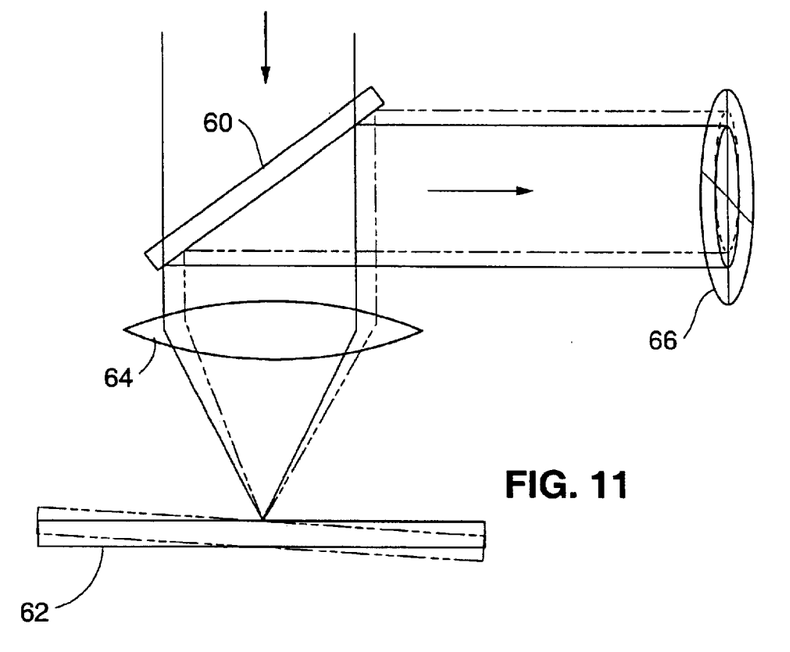
FIG. 11 shows a system for detecting sample tilt.

Since variations in the tilt of the sample surface at the milli-degree level are almost inevitable, it is necessary to have some means of dealing with tilt—especially pitch. FIG. 11 illustrates a preferred tilt detection scheme.

As depicted in FIG. 11, a laser beam is split by a beam splitter 60 oriented at a 45° angle. Part of the beam continues toward the sample 62 and is focused to a point by a lens 64. A reflected beam reflects from the sample 62 and passes back up through the same focusing optics. Part of the reflected beam is reflected by the beam splitter 60 to a position sensitive detector 66 which may preferably be a quad cell photodiode detector. A change in the sample orientation (shown by the dotted lines) causes the return beam to shift. This displacement can be measured quantitatively with the quad cell photodiode 66. The advantages of this method include its non-contact nature, high accuracy (determined by the focal length of the lens 64 and the sensitivity of the quad cell 66), and the fact that it can be conducted concurrently with XRR measurements because the quad cell detector 66 views the sample from above. With this method, tilts well below 0.001° may be measured.

Preferably the tilt detector described above may be calibrated using samples whose tilt is known. Alternatively, an approximate mathematical relationship between the readings of the quad cell detector and the sample tilt may be used to interpret the data. For this purpose it may be assumed that the light coming into the lens 64 of FIG. 11 is collimated and has uniform intensity over the illuminated circle on the lens (radius r), and that the lens aperture is larger than this illuminated spot. If the lens 64 has a focal length f and the wafer is tilted by a small angle d, then the reflected beam, 60, is shifted by a distance s on the quad cell detector 66, which distance s is given by:

$s=2 \times f \times d$ (where d is measured in units of radians).

For purposes of illustration it is convenient to consider the case where the tilt is in the plane of FIG. 11 (i.e. the axis of tilt rotation is about the normal to the paper), so that the reflected beam shifts upwards on the quad cell, 66, as shown by the dashed lines.

The quad cell is composed of 4 quadrants which each produce an output signal proportional to the intensity on the quadrant: Q1, Q2, Q3, & Q4 (quadrants 1 & 2 are on top; 3 & 4 are on bottom; and 1 & 4 are on the right side). We can define the vertical tilt signal as $Ty=(Q1+Q2-Q3-Q4)/(Q1+Q2+Q3+Q4)=[(top-bottom)/sum]$ (Here Ty means tilt about the vertical (y) axis to distinguish from tilt in orthogonal direction: Tx.)

When the quad cell is illuminated by a beam reflected from a non-tilted sample, each quadrant should produce signals of the same strength q0. In this case, the vertical tilt signal is $Ty=(q0+q0-q0-q0)(4 \times q0)=0$ For very small tilts that shift the beam upwards, the upper two quad signals increase and the lower two decrease. If the spot on the quad cell shifts up a distance s, then the increase in the signal Q1 is $\Delta Q1=(4 \times q0 \times s)/(\pi \times r)$; where $\pi=3.14159\ldots$ $=(8 \times f \times d \times q0)/(\pi \times r)$ (using the earlier equation for s).

In this case, the tilt signal becomes:

$Ty=\Delta Q1/q0=(8 \times f \times d)/(\pi \times r)$

This equation can be reversed to solve for the tilt angle d as a function of the measured tilt signal:

$d=(Ty*\pi*r)/(8 \times f)$.

The same kind of analysis may be applied in the case of an orthogonal tilt, Tx, or the case where there is both a vertical and orthogonal tilt.

Once the sample tilt has been independently measured, it is necessary to correct for the tilt. Either of two methods of correction may be used. In one method, the tilt may be corrected for in analyzing the data received from the X-ray detector. Alternatively, the orientation of the stage on which the sample rests may be actively controlled in order to reduce the tilt.

If the tilt of the stage is actively controlled, the tilt sensor reading may be used to purposely set the stage tilt to some non-zero angle. This could be useful in studying films with particularly large critical angles because tilting the stage would shift the incidence angle range to higher angles.

Figure 12:
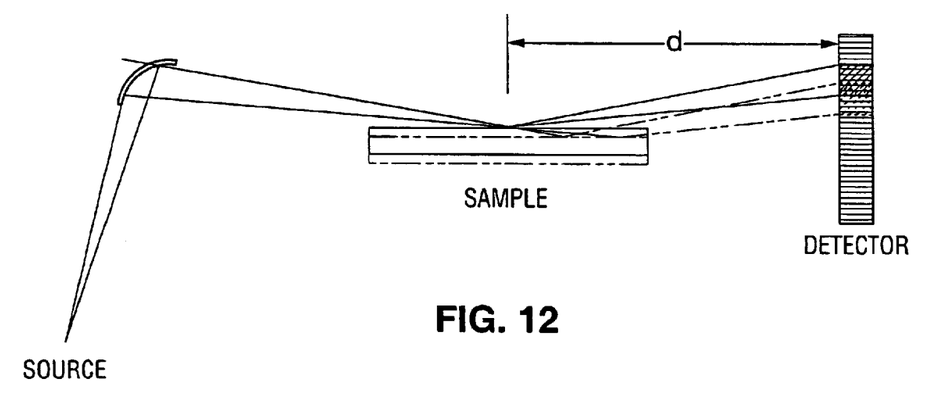
FIG. 12 shows how changes in sample height alter the relationship between X-ray angle of incidence and detector pixels in an XRR system.

Yet another aspect of the present invention concerns the calibration of the vertical position of the sample. Changes in this sample height lead to shifts in the location of the reflected beam as shown in FIG. 12. The shift of the reflected profile on the detector array is approximately 2δ, where δ is the focus error. and d is the distance from the focus to the detector. This results in an angular error of about δ/d, where d is the distance from the focus to the detector. (This is so because the zero angle is interpreted to be the midpoint between the incident and reflected beams.) For systems designed to measure 8" wafers, d could be as small as about 5" which means that for every 10 microns of focus error, an angular error of about 5 milli-degrees is introduced. Errors of this magnitude may alter the thickness readings by several angstroms and constitute a major limitation on measurement accuracy.

Figure 13:
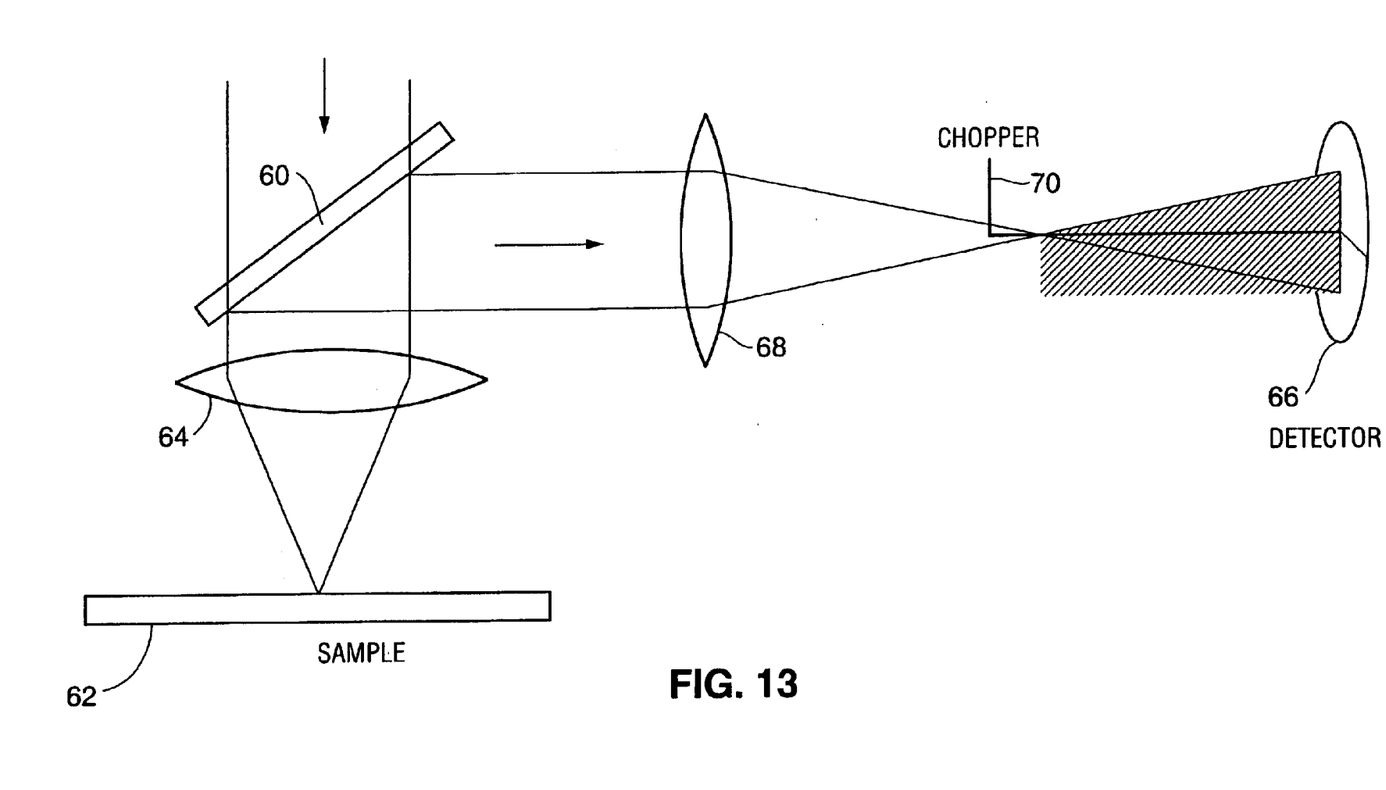
FIG. 13 a system for detecting changes in the sample height.

The present invention provides a method of controlling this source of error by quickly and accurately bring the XRR system into focus. This method for autofocusing works by measuring the collimation of a beam reflected from the sample surface through a focusing lens as shown in FIG. 13. The assignee of the present invention has previously employed a similar methodology for measuring both the tilt of the sample and the vertical position of the sample in the context of prior art light-based beam profile reflectometry and beam profile ellipsometry (see U.S. Pat. No. 5,042,951; U.S. Pat. No. 5,412,473; and PCT publication WO 92/08104. However, the inventors believe that they are the first to recognize that such a methodology could be used to solve the distinct problems characteristic to the proper calibration and operation of an X-ray reflectometry system.

As depicted in FIG. 13, a laser beam is split by a beam splitter 60 oriented at a 45° angle. Part of the beam continues toward the sample 62 and is focused to a point by a lens 64. A reflected beam reflects from the sample and passes back up through the same focusing optics. Part of the reflected beam is reflected by the beam splitter 60 and is focused by a second focusing lens 68. This second lens 68 brings the reflected beam into focus near a spinning knife edge or "chopper" 70, located in the focal plane of the lens 68. The location of this secondary focus is, in turn, dependent on the height of the sample. As the sample moves up, for instance, the secondary focus moves downstream. The direction and speed of the chopper's shadow is detected by a position sensitive detector 66 which may preferably be a quad cell photodiode detector. If the chopper is not located at the focus, one side or the other of the quad cell will be darkened first by the shadow of the chopper, depending on which side of the focus the chopper is located. By measuring the movement of the chopper's shadow, it is possible to calculate both the position of the secondary focus relative to the position of the chopper 70 and the sample height.

The precision of this method depends on the focal lengths and apertures of the various components and increases with the magnification of the lenses used.

The autofocus signal produced by the above described detector scheme may be defined as the timing difference Δt between the time when the top of the detector is shadowed and the time when the entire detector is shadowed. Δt can be positive or negative depending on whether the sample surface is above or below the focus. The sensitivity of the system S can be defined as the measured time gap for a given focus error:

$S=\Delta t/\Delta z$, where $\Delta z$ is the distance of the objective lens 64 from correct focus. (Like $\Delta t$, $\Delta z$ may be positive or negative.)

If the objective lens 64, has a focal length f1, and second lens 68, has a focal length of f2, and the beam incident on the first lens is collimated and has a radius of r, then the sensitivity S of the autofocus detector to small focus errors is given by $$S=2\times r\times f2/(f1\times f1).$$

From these equations it is possible to calculate $\Delta z$ given knowledge of $\Delta t$ and the parameters r, f1, and f2. Given $\Delta z$, the distance of the objective lens 64 from correct focus, an appropriate adjustment in the relative sample height may be made.

The scope of the present invention is meant to be that set forth in the claims that follow and equivalents thereof, and is not limited to any of the specific embodiments described above.

What is claimed is:

1. A method of measuring X-ray reflectivities of a thin film layer on the surface of a sample comprising the steps of:

generating a probe beam of X-rays;

focusing said probe beam on the surface of said sample such that various X-rays within the focused probe beam create a range of angles of incidence with respect to said surface;

measuring the intensity of various X-rays as a function of position within the probe beam as reflected with the positions of the X-rays within said reflected probe beam corresponding to specific angles of incidence with respect to said surface; and comparing the measurements of the intensity of the various X-rays within said reflected probe beam to corresponding measurements of an unattenuated probe beam made with the sample removed from the X-ray pathway.

2. A method as recited in claim 1, wherein said corresponding measurements of an unattenuated probe beam are made using an X-ray detector located at least in part below the plane of the sample.

3. A method as recited in claim 1, wherein said corresponding measurements of an unattenuated probe beam are made using an X-ray detector located both above and below the plane of the sample.

4. A method as recited in claims 1, 2, or 3, further wherein said measurements of the intensity of the various X-rays within said reflected probe beam are normalized by dividing by said corresponding measurements of the unattenuated probe beam made with the sample removed from the X-ray pathway.

5. A method as recited in claims 1, 2, or 3, further wherein the correspondence between the reflected probe beam and the unattenuated probe beam is obtained by locating a point of symmetry for the two probe beams within the region of small angles of incidence to the plane of the sample such that X-ray reflection from the sample is nearly total.

6. A method of measuring the characteristics of a thin film layer on the surface of a sample comprising the steps of:

generating a probe beam of X-rays;

focusing said probe beam on the surface of said sample such that various X-rays within the focused probe beam create a range of angles of incidence with respect to said surface;

measuring the intensity of various X-rays as a function of position within the probe beam as reflected with the positions of the X-rays within said reflected probe beam corresponding to specific angles of incidence with respect to said surface;

comparing the measurements of the intensity of the various X-rays within said reflected probe beam to corresponding measurements of an unattenuated probe beam made with the sample removed from the X-ray pathway; and determining the characteristics of said thin film layer based upon the intensity measurements.

7. A method as recited in claim 6, wherein said corresponding measurements of an unattenuated probe beam are made using an X-ray detector located at least in part below the plane of the sample.

8. A method as recited in claim 6, wherein said corresponding measurements of an unattenuated probe beam are made using an X-ray detector located both above and below the plane of the sample.

9. A method as recited in claims 6, 7, or 8, further wherein said measurements of the intensity of the various X-rays within said reflected probe beam are normalized by dividing by said corresponding measurements of the unattenuated probe beam made with the sample removed from the X-ray pathway.

10. A method as recited in claims 6, 7, or 8, further wherein the correspondence between the reflected probe beam and the unattenuated probe beam is obtained by locating a point of symmetry for the two probe beams within the region of small angles of incidence to the plane of the sample such that X-ray reflection from the sample is nearly total.

\* \* \* \* \*